United States Patent [19]

Manning

[11] 4,313,016
[45] Jan. 26, 1982

[54] ISOBUTENE REMOVAL FROM C4 STREAMS

[75] Inventor: Harold E. Manning, Houston, Tex.

[73] Assignee: Petro-Tex Chemical Corporation, Houston, Tex.

[21] Appl. No.: 199,842

[22] Filed: Oct. 23, 1980

[51] Int. Cl.$^3$ ............... C07C 7/148; C07C 7/177; C07C 2/04
[52] U.S. Cl. ............... 585/832; 585/510; 585/515; 585/921; 585/800
[58] Field of Search ............... 585/832; 585/510

[56] References Cited

U.S. PATENT DOCUMENTS

| | | | |
|---|---|---|---|
| 3,518,323 | 6/1970 | Pine et al. | 260/683.15 |
| 3,531,539 | 9/1970 | Tidwell | 260/677 |
| 3,546,317 | 12/1970 | Gislon et al. | 260/683.15 |
| 3,823,198 | 7/1974 | Goldsby | 260/677 A |
| 3,832,418 | 8/1974 | Bercik et al. | 260/683.15 R |
| 4,065,512 | 12/1977 | Carts | 260/641 |
| 4,100,220 | 7/1978 | Bowmen et al. | 260/683.15 R |
| 4,215,011 | 7/1980 | Smith | 252/426 |
| 4,242,530 | 12/1980 | Smith | 585/832 X |

OTHER PUBLICATIONS

Haag, "Kinetics and Catalysis", 63, No. 73, pp. 140–147.

*Primary Examiner*—Paul F. Shaver
*Attorney, Agent, or Firm*—Kenneth H. Johnson

[57] ABSTRACT

The isobutene in C$_4$ hydrocarbon streams containing from 0.5 to 5% isobutene and n-butenes is reduced preferably to a level of 0.2 mole % or less by passing the feed stream at LHSV 2.5 to 12 in liquid phase through a fixed-bed cation exchange resin catalyst in a tubular reactor with a water heat exchange medium maintained at a temperature of 50° to 80° C., whereby the isobutene is oligomerized and easily separated from the remaining C$_4$'s by fractionation.

11 Claims, 3 Drawing Figures

ISOBUTENE REMOVAL FROM C4 STREAMS

BACKGROUND OF THE INVENTION

1. Field of the Invention

The present invention relates to the separation of small quantities of isoolefins from streams containing mixtures of an isoolefin and the corresponding normal olefin. The present invention is especially useful for the separation of isobutene from streams containing n-butenes to obtain high purity n-butenes. More particularly, the present invention is useful for removing isobutene from butene-1 containing streams.

2. Prior Art

Isoolefins of 4 carbon atoms are difficult to separate from the corresponding normal olefin by simple fractionation because of the closeness of their boiling points. In the prior art processes that are generally practiced commercially, the isoolefin is selectively absorbed by sulfuric acid and the resulting isoolefin-containing sulfuric acid extract is then diluted and heated or treated with steam to separate the isoolefin.

The n-butenes are required in pure form for homopolymerization and as feeds for the oxidative production of butadiene. Isobutene and diisobutene are of significant value having diverse applications, for example, isobutene is one of the comonomers for butyl rubber and diisobutene is an intermediate in the preparation of detergents. The isobutene oligomers are useful as polymer gasoline. One manner of separating these components is to pass the mixture through a cold acid extraction procedure wherein the stream is fed into a bath of sulfuric acid. Separation is achieved by virtue of the solubility of the isobutene in the sulfuric acid, the n-butenes and other hydrocarbons present passing overhead, for example as shown in U.S. Pat. Nos. 3,546,317 and 3,823,198.

Other processes have used various catalysts for converting the isobutene to diisobutene which is then easily separated from the product stream. For example, a process using a molecular sieve and elevated temperatures is disclosed in U.S. Pat. No. 3,531,539; U.S. Pat. No. 3,518,323 employs a supported nickel oxide catalyst; and U.S. Pat. No. 3,832,418 employs a Group VI or VIII metal deposited on acidic, amorphous silica-alumina in the same manner.

More recently, U.S. Pat. No. 4,215,011 disclosed the use of acid cation exchange resin in a heterogenous combination reaction-distillation system for the selective dimerization of isobutene in the presence of normal butenes. The reaction is highly preferential for the reaction of isobutene with itself although some codimer between n-butenes and isobutene are formed and provides a means to separate isobutene from a C4 stream.

Although the present process is suited to treat other isoolefin-normal olefins mixtures, it is of particular significance for the recovery of product streams with sufficiently low levels of isobutene to be processable to obtain useable n-butenes; and particularly butene-1, which is the n-butene isomer employed in homopolymerization to produce polybutene; or copolymerization with other monomers; and as a feed for oxidative dehydrogenation to produce butadiene-1,3.

It is a principal feature of the present process that the amount of isobutene in the stream is reduced to levels sufficiently low to allow further separation of a useful butene-1 product. It is another feature of the present process that a very useful product is produced from the isobutene, i.e., polymer gasoline. It is a particular advantage of the present process that it may be operated to obtain the above results with a limited loss of butene-1.

Another feature of the present process is the substantial energy saving over the cold acid method of isobutene removal and a reduction in capital expenditures to replace and/or repair processing equipment that has failed due to the corrosive nature of the sulfuric acid.

SUMMARY OF THE INVENTION

The present invention is a process for removing isobutene from a feed stream comprising predominately $C_4$ hydrocarbons and containing isobutene and n-butenes, said isobutene being present in an amount of 0.5 to less than 5 mole percent comprising:

(a) contacting said feed stream in liquid phase with a fixed bed cation exchange resin in a reactor at a temperature of from 50° to 80° C., preferably up to 70° C., said feed stream being fed at a rate of a liquid hourly space velocity of from about 0.5 to 12, preferably at least 2.5, (b) reacting the isobutene to form oligomers thereof having number average molecular weight of $C_{16}$ hydrocarbons or less to form a product stream comprising said $C_4$ hydrocarbons and oligomers and having a substantially lower amount of isobutene than said feed stream and, (c) removing said product stream from said reactor.

The product stream thus produced is then processed further in a preferred embodiment by fractionating said product stream to recover an overhead $C_4$ fraction having an isobutene content substantially lower than said feed stream and a bottoms fraction consisting essentially of said oligomers.

More preferably the present invention is a process for recovering a product stream having less than 0.2 volume percent of isobutene therein from a feed stream as defined and containing at least 50 percent of the butene-1 of said feed stream and more preferably at least 80 percent of the butene-1 of the original feed stream.

The conditions of space velocity and temperature are adjusted within the ranges specified to obtain maximum isobutene and minimal loss of butene-1 by isomerization or the loss of normal butenes by reaction.

DETAILED DESCRIPTION OF THE INVENTION AND PREFERRED EMBODIMENTS

Figure 1:
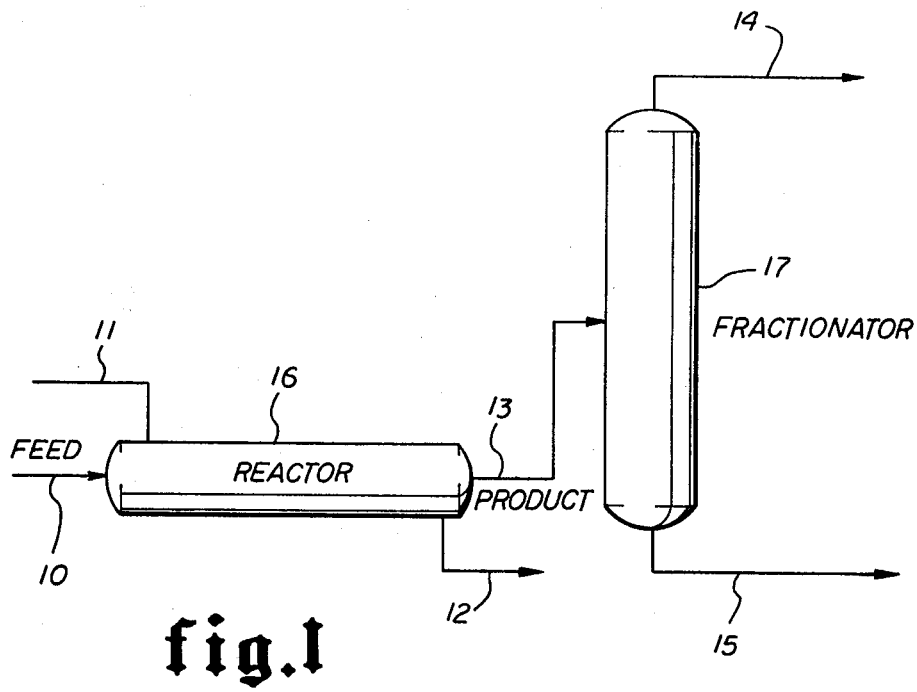
FIG. 1 is a schematic depiction of a preferred embodiment of the present process.

The principal consideration in treating a $C_4$ stream containing isobutene, butene-1, butene-2, normal butane and isobutane in the present process is the removal of isobutene therefrom. Complete removal would be most desirable; however, in practice that is not possible without serious detriment to the remainder of the feed stream. Hence, in the present specification and claims an overhead $C_4$ fraction containing less than 0.2 mole percent of isobutene is that determined to be suitable for further processing to produce a useable butene-1 fraction.

The C$_4$ feed streams may have small amounts of C$_3$ and C$_5$. However, these are usually less than 1.0 volume percent of the total stream and are of no consequence. Further, the degree of skill employed in operating refineries now makes possible C$_4$ streams substantially free of lower and higher hydrocarbons.

In carrying out the present process, it was determined that temperature of cooling medium (which reflects the exotherm in the catalyst bed) was of particular importance. It was found that operating the process at cooling temperatures below about 55° C., e.g., 40° C. or 50° C. failed to reduce the isobutene content to the requisite 0.2 volume percent or less, for more than a few days on stream, even at longer residence times. Higher temperatures favor the oglimerization of the isobutene. The temperature range of 50° to 80° C. reflects the operable range which may be used to carry out the reaction over a useful time trend of the catalyst which tends to decline in activity, as higher polymers are deposited thereon. That is, with a fresh catalyst as low a temperature as possible would be maintained until a decline in the isobutene removal required higher temperatures.

As stated, the primary purpose of the present process is the removal of isobutene from the feed stream to the 0.2 or less mole percent level. However, higher temperatures than required for this are detrimental in that they favor loss of the desired butene-1 by (1) isomerization to butene-2, (2) copolymerization with the isobutene and/or (3) polymerization of the n-butenes. Thus, the operation of the present process at any higher temperature within the recited range than necessary to reduce the isobutene content below 0.2 vol. % is counter productive to the butene-1 content thereof. The determination of the upper operating temperature is readily made by the operation of the process and routine sampling based on the extent the operator is willing to sacrifice butene-1 for isobutene removal. Beyond the upper limit of 80° C., even with the reduced activity of the catalyst, the rate of butene-1 loss, e.g., by isomerization would not be acceptable according to the present invention. Also at higher temperatures the normal butenes react, not only with isobutene, but with each other to form dimers and higher oligomers.

The deactivated catalyst is not lost and is easily returned to its original level of activity (allowing for some loss in activity as experienced with all catalysts regardless of regeneration treatment) by removing the built up polymer. This is achieved by discontinuing the C$_4$ feed and passing a solvent for the oligomer through the reactor. Any of the conventional solvents for thermoplastic hydrocarbon polymers may be used, so long as they are not activated by the resin catalyst. For example, the various hydrocarbons, including, butane, pentane, hexane, benzene, toluene, xylene and the like may be used. Diisobutylene and the oligomers from the reaction are also useful and completely non-contaminating for this purpose. The solvents are employed with the heat exchange medium used to lower the temperature, for example to around 40° C. for a determinable period, during which the solvent in liquid phase is passed through the fixed bed of resin. The feed stream is reinstituted after the operator determines the polymer is sufficiently removed.

The isomerization of butene-1 was found to be effected by the residence time of the feed stream in the catalyst bed. For example, at a temperature of about 60° C. (fresh catalyst) a reduction of the isobutene content in the product stream to 0.2 vol. % or less is still obtainable with only about 10% loss in butene-1 at LHSV 12.

Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Pat. No. 908,247).

The ion exchange resin is preferably used in a granular size of about 0.25 to 1 mm, although particles from 0.15 mm up to about 2 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium. Preferred catalysts have surface areas of from about 20 to 600 square meters per gram.

Referring to FIG. 1, a schematic representation of a preferred embodiment of the present process is shown. The isobutene containing C$_4$ feed stream enters reactor 16 via line 10 where it is contacted with the resin catalyst (not shown). The reaction temperature is maintained constant by means of a fluid medium entering the reactor through line 11 where it is in indirect contact with the catalysts to either remove heat or supply heat, such as on start-up. The fluid medium exits the reactor via line 12 and is treated elsewhere as required to maintain the desired temperature in the reactor.

The fluid medium can be any fluid capable of providing indirect heat exchange with the fixed bed catalyst. Water is particularly preferred because of the operational temperature range for the present process. However, air or organic liquids could be employed for this purpose.

In the reactor the $C_4$ stream contacts the catalyst and isobutene is preferentially reacted with itself to form a mixture of dimers, trimers and tetramers of number average molecular weight of a $C_{16}$ hydrocarbon or less. This product passes via line 13 into fractionator 17 where by simple distillation the product is split to recover the oligomer as a bottoms fraction removed through line 14 and the $C_4$ as an overhead, removed through line 15, hence to further treatment for further separation of the remaining $C_4$'s.

Figure 2:
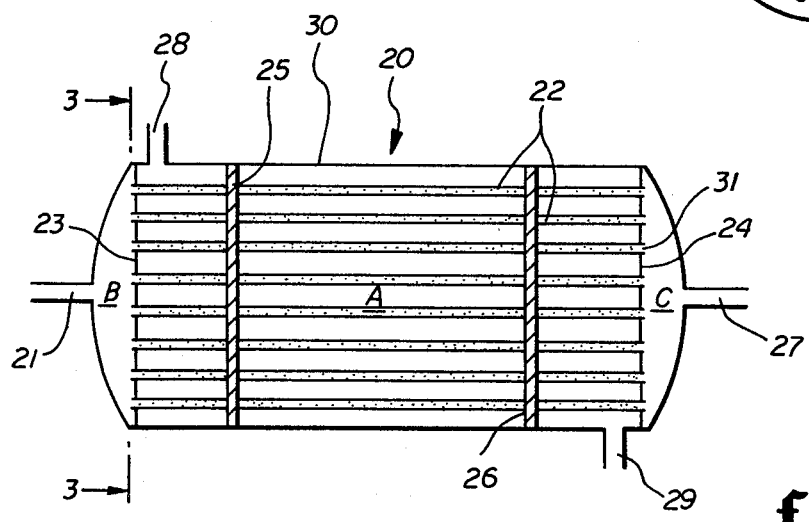
FIG. 2 is a cross sectional elevation of a reactor for carrying out the process of the present invention.

The heat exchange fluid is in indirect contact with the fixed catalyst bed. FIG. 2 shows a conventional and preferred means of obtaining this contact. Reactor 20 is a multitube reactor comprising a shell 30 having mounted therein tubes 22, usually of ⅛ to 2 inches outside diameter. The reactor is shown horizontally. However, it could be vertical or inclined. The tubes 22 are mounted through plates 25 and 26 respectively and attached at each end to header plates 23 and 24 which are to prevent fluid communication between the area adjacent to the tubes A, the feed entry area B, and product exit area C. The tubes 22 are in liquid communication with areas B and C. A feed entry pipe 21 is located on the B area and a product exit pipe 27 is located on the C area. Heat exchange medium is provided into the A area via pipe 28 and an exit is provided via pipe 29.

Figure 3:
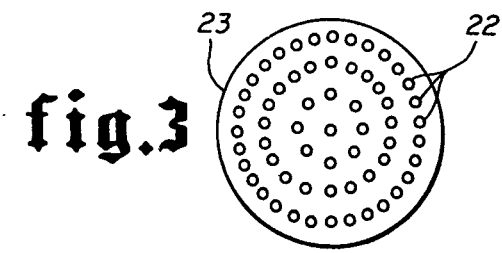
FIG. 3 is a cross sectional view of the reactor of FIG. 2 taken along line 3—3.

The tubes 22 are packed with the cation exchange resin in granular form 31 and means such as screen (not shown) are fitted to each tube to retain the catalyst therein. FIG. 3 shows an arrangement of tubes 22 in header plate 23.

The reaction of isobutene with itself is exothermic and the heat exchange medium, e.g., water provides the means for controlling the reaction to favor a selective reaction of isobutene with itself to form oligomers rather than the production of cooligomers with the n-butenes or higher polymers, i.e., a runaway reaction in the absence of such control.

The reaction is carried on in liquid phase and sufficient pressure is maintained on the system to keep the $C_4$ stream in liquid phase under the conditions of reaction, i.e., about 35 to 300 psig.

The term liquid hourly space velocity (LHSV) means the liquid volumes of hydrocarbon per volume of reactor containing catalyst per hour.

The $C_4$ feed stream should be free or substantially free of catalyst poisons, such as metal cations or basic nitrogen compounds, e.g., $NH_3$ or dimethylamane. Water or methanol may be present in small amounts, insufficient to form an entrained second phase, to serve as a catalyst modifier.

EXAMPLES

In the following examples, the reactor consisted of a preheat section of coiled ⅛" OD stainless steel tubing connected to ¼" OD stainless tubing packed with 25 cc of dry resin as described. Both sections were immersed in a water bath of controlled temperature which is the temperature reported. A back-pressure regulator located downstream of the catalyst bed was used to maintain the desired pressure in the reactor system. Product effluent was collected in a stainless steel vessel, downstream of the pressure regulator. After a sufficient volume of effluent had been collected for analysis, the contents of the SS vessel were transferred to a tared and evacuated Pyrex-bottle fitted with a rubber septum mounted in a perforated metal cap. A 20-gauge needle attached to the SS vessel was inserted through the rubber septum of the bottle and the reaction products were collected for reweighing. The contents of the Pyrex bottle were then evaporated at room temperature and later at 90° F. via in transfer line into a second evacuated bottle immersed in a mixture of acetone and solid $CO_2$. Separation of the lower boiling-point unreacted $C_4$ hydrocarbons from the higher boiling-point oligomerized products was thus effected and the weight percent of oligomers calculated. The composition of each of the two hydrocarbon fractions was determined chromatographically.

The following abbreviations are used in the examples:

| | | |
|---|---|---|
| Propylene | = | $C_3=$ |
| Isobutane | = | $i$-$C_4$ |
| Normal-butane | = | $n$-$C_4$ |
| Butene-1 | = | B-1 |
| Butene-2 | = | B-2 |
| Butene-2(trans) | = | B-2-t |
| Butene-2(cis) | = | B-2-c |
| Isobutene | = | $i$-$C_4=$ |
| Butadiene | = | Bd |
| Liquid volume | = | LV |

EXAMPLE 1

The conditions and results are reported in TABLE I.

TABLE I

Catalyst[1]: Amberlyst 15
Conditions: LHSV = 5.0, Pressure = 100 psig.
Feed: Hydrocarbons from Plant

| Reaction Temp. °C. | Hrs. on Stream | $C_4$ Product Analysis (Chromatographic %)[2] | | | | | Wt. % Oligomers Produced |
|---|---|---|---|---|---|---|---|
| | | i-$C_4$ | n-$C_4$ | B-1 | i$C_4=$ | B-2-t | B-2-c | |
| — | Feed Analysis | 0.03 | 7.40 | 83.00 | 2.13 | 6.97 | 0.46 | — |
| 60 | 15 | — | 7.51 | 59.87 | <0.1[3] | 18.69 | 13.94 | 6.6[4] |
| 50 | 17 | — | 7.54 | 78.35 | <0.1 | 10.07 | 4.00 | 4.0 |
| 40 | 19 | — | 7.27 | 82.53 | 0.34 | 8.25 | 1.61 | 1.9 |
| 60 | 39 | — | 7.45 | 58.80 | <0.1 | 19.77 | 14.00 | 7.4 |
| 60 | 63 | — | 7.51 | 64.94 | <0.1 | 16.36 | 11.14 | 6.6 |
| New Feed | Feed Analysis | 0.06 | 6.53 | 84.03 | 2.23 | 6.71 | 0.45 | 0.03 |
| 50 | 71 | — | 6.87 | 79.00 | <0.1 | 9.86 | 4.27 | 4.4 |
| 50 | 75 | 0.05 | 6.79 | 80.73 | 0.52 | 8.83 | 3.09 | 3.0 |
| 50 | 127 | — | 6.69 | 81.20 | 0.94 | 8.50 | 2.67 | — |
| 60 | 130 | 0.07 | 6.83 | 73.60 | <0.1 | 12.15 | 7.35 | 4.6 |

[1]Wet resin washed with acetone and dried before loading into reactor.
[2]Results are approximate LV %.
[3]No detectable conc. of i-$C_4=$ (<0.1%).
[4]Oligomer analysis (LV %) = 22.3% Dimer, 39.9% Codimers, 37.7% Trimers.

EXAMPLE 2

This example demonstrates the process at 60° C. The conditions and results are reported in TABLE II.

TABLE II

Catalyst[1]: Amberlyst 15
Conditions: LHSV = 5, Pressure—100 psig,
Reaction Temp. = 60° C.
Feed: C$_4$ Hydrocarbons from Plant

| Hrs. On Stream | C$_4$ Product Analysis (Chromatographic %)[2] | | | | | |
|---|---|---|---|---|---|---|
| | i-C$_4$ | n-C$_4$ | B-1 | i-C$_4$= | B-2-t | B-2-c |
| Feed Analysis | — | 3.92 | 89.71 | 3.88 | 2.24 | 0.23 |
| 6 | — | 4.05 | 76.79 | <0.1[3] | 10.47 | 8.65 |
| 27 | — | 4.11 | 55.13 | <0.1 | 22.50 | 18.26 |
| 51 | — | 4.18 | 51.54 | <0.1 | 24.52 | 19.75 |
| 75 | 0.04 | 4.00 | 64.21 | <0.1 | 17.07 | 14.67 |
| 99 | 0.02 | 4.04 | 67.57 | <0.1 | 15.04 | 13.29 |
| New Feed Analysis | — | 6.71 | 81.16 | 2.41 | 8.73 | 0.97 |
| 132 | — | 6.86 | 67.14 | <0.1 | 15.45 | 10.49 |
| 156 | — | 6.87 | 69.94 | <0.1 | 13.97 | 9.05 |
| 204 | — | 6.97 | 71.48 | <0.1 | 13.25 | 8.03 |
| New Feed Analysis | 0.02 | 7.33 | 81.08 | 2.29 | 8.25 | 0.99 |
| 236 | 0.07 | 7.73 | 71.47 | <0.1 | 13.52 | 7.19 |
| New Feed Analysis | 0.10 | 8.03 | 78.43 | 3.21 | 9.25 | 0.98 |
| 315 | 0.09 | 8.17 | 70.59 | <0.1 | 13.87 | 7.24 |
| New Feed Analysis | 0.14 | 8.29 | 77.87 | 2.95 | 9.61 | 1.11 |
| 364 | 0.11 | 7.98 | 72.07 | <0.1 | 13.23 | 6.58[4] |
| 412 | 0.12 | 8.50 | 72.83 | <0.1 | 12.98 | 5.57 |

[1] Wet resin washed with acetone and dried before loading into reactor.
[2] Results are approximate LV %.
[3] i-C$_4$= below limits of chromatographic detection; i.e., <0.1 LV %.
[4] Analysis of oligomers produced (LV %) = 52.86% Dimer, 29.08% Codimers, 18.06% Trimers.

EXAMPLE 3

This examples demonstrates various residence times. The conditions and results are reported in TABLE III.

TABLE III

Catalyst[1]: Amberlyst 15
Conditions: Pressure = 100 psig. Temperature = 60° C.
Feed: C$_4$ Hydrocarbons from Plant

| Reaction Temp, °C. | LHSV | C$_4$ Product Analysis, Liq. Vol. %[2] | | | | | | % Loss of B-1, (i-C$_4$= Free Basis) | Wt. % Oligomers Produced |
|---|---|---|---|---|---|---|---|---|---|
| | | i-C$_4$ | n-C$_4$ | B-1 | i-C$_4$= | B-2-t | B-2-c | | |
| Feed Analysis | | 0.10 | 2.95 | 93.24 | 1.15 | 2.22 | 0.34 | — | — |
| Feed Analysis, iC$_4$= Free Basis | | 0.10 | 2.98 | 94.32 | <0.1[3] | 2.25 | 0.34 | — | — |
| 60 | 4.6 | 0.09 | 3.09 | 67.52 | <0.1 | 15.96 | 13.35 | 28.4 | 3.74 |
| 60 | 6.0 | 0.07 | 3.07 | 73.92 | <0.1 | 12.41 | 10.53 | 21.6 | 3.29 |
| 60 | 7.5 | 0.08 | 3.05 | 77.32 | 0.05 | 10.62 | 8.89 | 18.0 | 2.83 |
| 60 | 8.9 | 0.08 | 3.04 | 80.23 | 0.09 | 9.07 | 7.49 | 14.9 | 2.54 |
| 60 | 10.4 | 0.08 | 3.01 | 82.14 | 0.14 | 8.08 | 6.55 | 12.8 | 2.43 |

[1] Wet resin washed with acetone and dried before loading into reactor.
[2] Approximate LV %.
[3] No dedectible i-C$_4$= (<0.1%).

The invention claimed is:

1. A process for removing isobutene from a feed stream comprising predominately C$_4$ hydrocarbons and containing isobutene and n-butene, said isobutene being present in an amount of from about 0.5 to 5 mole percent comprising:
   (a) contacting said feed stream in liquid phase with a fixed bed of sulfonic acid group containing cation exchange resin in a reactor at a temperature of from 50° to 80° C., said feed stream being fed at a rate of a liquid hourly space velocity from about 2.5 to 12,
   (b) reacting the isobutene to form oligomers thereof having number average weight of C$_{16}$ hydrocarbons or less to form a product stream comprising said C$_4$ hydrocarbons and oligomers and having less than 0.2 vol. % isobutene therein, and
   (c) removing said product stream from said reactor.

2. The process according to claim 1 wherein said product stream is fractionated to recover an overhead C$_4$ fraction having an isobutene content substantially lower than said feed stream and a bottom fraction consisting essentially of said oligomers.

3. The process according to claim 1 wherein said reactor has a heat exchange medium associated therewith.

4. The process according to claim 3 wherein said reactor comprises one or more small diameter tubes containing said catalyst surrounded by said heat exchange medium.

5. The process according to claim 1 wherein said feed stream is fed to the reactor at a pressure in the range of about 35 to 300 psig.

6. A process according to claim 1 or 2 wherein said product stream contains at least 50 mole percent of the butene-1 of said feed stream.

7. The process according to claim 6 wherein said product stream contains at least 80 mole percent of the butene-1 of said feed stream.

8. The process according to claim 1 wherein said catalyst is in the form of granular particles having a surface area of 20 to 600 square meters per grams.

9. The process according to claim 4 wherein said tubes are from ⅛ inch to 2 inches outside diameter.

10. The process according to claim 9 wherein said heat exchange medium is water.

11. The process according to claim 10 wherein the temperature is in the range of 60° to 70° C.

* * * * *